(12) United States Patent
Habu et al.

(10) Patent No.: US 8,231,534 B2
(45) Date of Patent: Jul. 31, 2012

(54) ULTRASONIC TRANSMITTER/RECEIVER DEVICE, ULTRASONIC PROBE AND ULTRASONIC DIAGNOSTIC APPARATUS

(75) Inventors: Takeshi Habu, Hachioji (JP); Yuji Hosoi, Hachioji (JP); Takayuki Sasaki, Hachioji (JP); Toshihisa Takeyama, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 248 days.

(21) Appl. No.: 12/598,951

(22) PCT Filed: Apr. 23, 2008

(86) PCT No.: PCT/JP2008/057843
§ 371 (c)(1),
(2), (4) Date: Nov. 5, 2009

(87) PCT Pub. No.: WO2008/139869
PCT Pub. Date: Nov. 20, 2008

(65) Prior Publication Data
US 2010/0210949 A1 Aug. 19, 2010

(30) Foreign Application Priority Data

May 10, 2007 (JP) ................................. 2007-126087

(51) Int. Cl.
*A61B 8/00* (2006.01)
(52) U.S. Cl. ......... 600/459; 600/437; 29/25.35; 29/594; 310/311
(58) Field of Classification Search .................. 600/437, 600/459; 29/25.35, 594; 310/311, 322, 334; 73/514.34
See application file for complete search history.

(56) References Cited

U.S. PATENT DOCUMENTS 5,150,715 A * 9/1992 Ishiguro et al. ............... 600/463
5,295,487 A 3/1994 Saitoh et al.
(Continued)

FOREIGN PATENT DOCUMENTS

JP 07-170600 7/1995
(Continued)

OTHER PUBLICATIONS

International Search Report of International Application No. PCT/JP2008/057843, mailed on May 27, 2008 (2 pages).

(Continued)

*Primary Examiner* — Brian Casler
*Assistant Examiner* — Amanda Lauritzen
(74) *Attorney, Agent, or Firm* — Finnegan, Henderson, Farabow, Garrett & Dunner, L.L.P.

(57) ABSTRACT

The ultrasonic transmitter/receiver device comprises a transmission section which transmits ultrasonic waves generated by a piezoelectric element when a transmission signal is inputted, a reception section which is superposed directly or indirectly on the transmission section and outputs a reception signal generated by a piezoelectric element when ultrasonic waves are received, a pair of a transmission signal wire and a transmission grounding wire for supplying the transmission signal to the transmission section, and a pair of a reception signal wire and a reception grounding wire for taking the reception signal from the reception section. The transmission grounding wire and the reception grounding wire are used in common as a common grounding wire. The common grounding wire and the transmission signal wire, and further the common grounding wire and the reception signal wire are disposed on different side surfaces of the transmission section and the reception section superposed with each other.

7 Claims, 8 Drawing Sheets

U.S. PATENT DOCUMENTS

| | | |
|---|---|---|
| 5,389,848 A | 2/1995 | Trzaskos |
| 6,552,471 B1 | 4/2003 | Chandran et al. |
| 2002/0007118 A1 | 1/2002 | Adachi et al. |
| 2002/0075099 A1 | 6/2002 | Itasaka et al. |

FOREIGN PATENT DOCUMENTS

| | | |
|---|---|---|
| JP | 10-126202 | 5/1998 |
| JP | 11-155863 A | 6/1999 |
| JP | 11-276478 | 10/1999 |
| JP | 2003-305043 | 10/2003 |
| JP | 2004-208918 | 7/2004 |

OTHER PUBLICATIONS

Extended European Search Report of International Application No. PCT/JP2008/057843, mailed on Feb. 10, 2012 (8 pages).

* cited by examiner

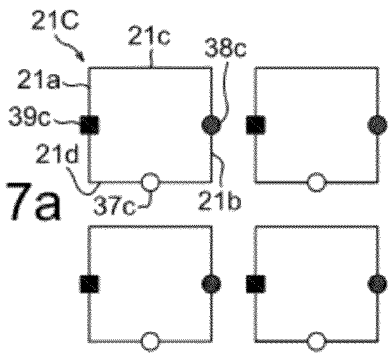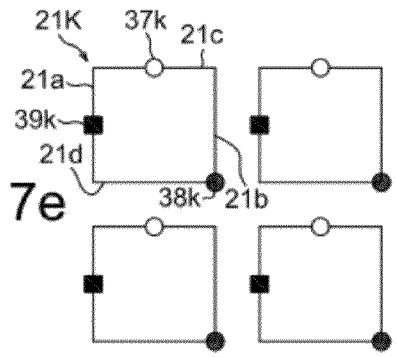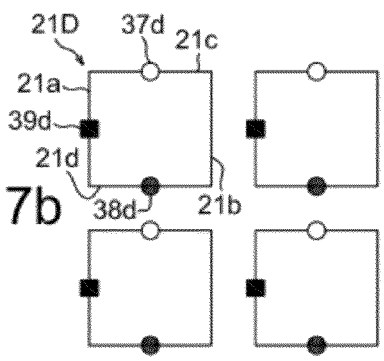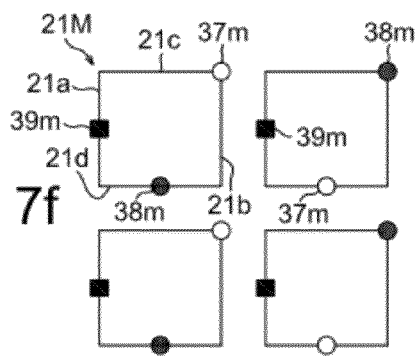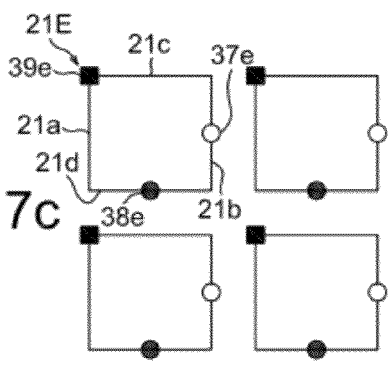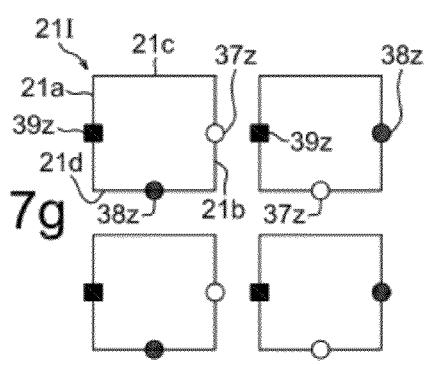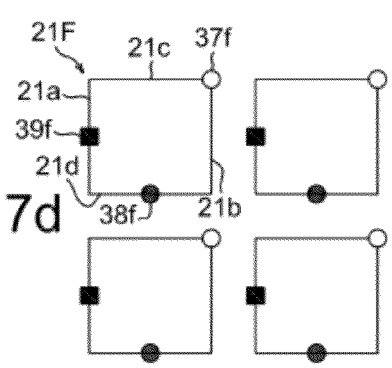

ULTRASONIC TRANSMITTER/RECEIVER DEVICE, ULTRASONIC PROBE AND ULTRASONIC DIAGNOSTIC APPARATUS

FIELD OF THE INVENTION

The present invention relates to an ultrasonic transmitter/receiver device capable of transmitting and receiving ultrasonic waves, and an ultrasonic probe and ultrasonic diagnostic apparatus using the same.

BACKGROUND OF THE INVENTION

An ultrasonic wave is commonly defined as a wave of 16,000 Hz or more. It allows the internal state of an object to be checked in a nondestructive manner, without the interior being harmed, and is utilized in various fields for examination of a defect, diagnosis of a disease and others. One of the applications of an ultrasonic wave is found in an ultrasonic diagnostic apparatus, wherein the interior of a test object is scanned by an ultrasonic wave, and the internal state of the test object is formed into an image, based on the reception signal generated from reflected ultrasonic wave (echo) from inside the test object. This ultrasonic diagnostic apparatus uses an ultrasonic probe for transmitting and receiving the ultrasonic wave to and from the test object. This ultrasonic probe is formed, for example, of a two-dimensional array of ultrasonic transmitting/receiving elements. These ultrasonic transmitting/receiving elements are provided with piezoelectric elements that cause a mechanical vibration and generate an ultrasonic wave, based on the transmission signal, and generate a reception signal by receiving the reflected wave of the ultrasonic wave produced by the mismatching of acoustic impedance inside the test object.

In recent years, efforts have been made to research and develop a harmonic imaging technique which, instead of using the frequency (fundamental frequency) component of the ultrasonic wave transmitted from the ultrasonic probe into the test object, employs the harmonic frequency component thereof to form an image of the internal state of the test object. This harmonic imaging technique has various forms of advantages such as the contrast resolution enhanced by the improvement of the S/N ratio (signal-to-noise ratio) by the side lobe level that is smaller than the level of the fundamental frequency component, the lateral resolution improved by the beam width reduced by a higher frequency, the multiple reflection reduced by a smaller sound level and smaller fluctuation in the sound level at a short distance, and sensitivity in the depths allowed in a high level as compared to the case where a high frequency wave is used as the fundamental wave, because attenuation beyond the focus is on the level of that of the fundamental wave.

The ultrasonic probe for the harmonic imaging requires a wide range of frequency bands extending from the frequency of a fundamental wave to the frequency of a harmonic wave. The frequency-domain on the low frequency side is used for transmission to transmit the fundamental wave, and the frequency-domain on the high frequency side is used for reception to receive the harmonic wave. This ultrasonic probe for harmonic imaging is exemplified by the apparatus disclosed in the Patent Literature 1.

The ultrasonic probe disclosed in the Patent Literature 1 is applied to a test object, and receives the ultrasonic wave returned by reflection from inside the test object after having been sent into the test object. The ultrasonic probe includes a first piezoelectric layer that includes a plurality of arranged first piezoelectric elements having a predetermined first acoustic impedance. This first piezoelectric layer takes charge of transmission of the fundamental wave consisting of ultrasonic waves having a predetermined center frequency, toward the interior of a test object, and reception of the fundamental wave out of the ultrasonic wave having been returned by reflection from the inside of the test object. Further the ultrasonic probe includes a second piezoelectric layer that includes a plurality of arranged piezoelectric elements having a predetermined second acoustic impedance smaller than the first acoustic impedance. The aforementioned second piezoelectric layer is overlapped on the entire surface of the first piezoelectric layer on the side, the ultrasonic probe of which is applied to the test object, and is in charge of reception of the harmonic wave out of the ultrasonic wave having been returned by reflection from the inside of the test object. The ultrasonic probe disclosed in the Patent Literature 1 uses the aforementioned structure to transmit and receive ultrasonic waves in a wide frequency band.

Patent Literature 1: Japanese Unexamined Patent Application Publication No. Hei 11-276478

DISCLOSURE OF THE INVENTION

Problems to be Solved by the Invention

Incidentally, in the ultrasonic probe, each of the piezoelectric elements constituting an ultrasonic probe requires a set (a pair) of wires for supplying the transmission signal of the electric signal for generating an ultrasonic wave, and a set (a pair) of wires for picking up the reception signal of the electric signal generated by receiving the ultrasonic wave. Each piezoelectric element normally has a rectangular shape on the order of several millimeters, in planar view for example. A few thousand of these piezoelectric elements are arranged in a two-dimensional array at intervals of the order of submillimeters. Thus, a few thousand through tens of thousands of wires are arranged in a narrow space. This raises a problem with cross talk between these wires. Further, in the ultrasonic probe disclosed in Patent Literature 1, the second piezoelectric layer is placed on the top of the first piezoelectric layer. Thus, depending on the method of wire arrangement, the aforementioned wiring interval may be further reduced, and this raises a more serious problem with the cross talk between wires. Further, in the ultrasonic probe for harmonic imaging, for example, the harmonic waves of the fundamental wave such as the second, third and fourth harmonic waves are also received. This increases the frequency of the electric signal that is sent through these wires, with the result that this problem will be more serious.

If cross talk is caused between the wires, there will be a relative decrease in the amount of the reception signals generated by receiving the ultrasonic probe. This will result in the deterioration of the performances of the apparatus, such as a reduction in the sensitivity of the ultrasonic probe or a reduction in the width of the dynamic range.

In view of the problems described above, it is an object of the present invention to provide an ultrasonic transmitter/receiver device capable of minimizing cross talk between wires. Another object of the present invention is to provide an ultrasonic probe and an ultrasonic diagnostic apparatus provided with the aforementioned ultrasonic transmitter/receiver device.

Means for Solving the Problems

The present inventors have made concentrated study efforts to find out that the objects of the above can be achieved by the following invention. To be more specific, an ultrasonic transmitter/receiver device of an embodiment of the present invention includes a transmission section for transmitting the ultrasonic wave generated by the piezoelectric element when the transmission signal is inputted a reception section which is laid directly or indirectly on the transmission section and which is used to output the reception signal generated by the piezoelectric element when the ultrasonic wave is received, a set of transmission signal wire and grounding wire for transmission for supplying the transmission signal to the transmission section, and a set of reception signal wire and grounding wire for reception for picking up the reception signal from the reception section, wherein the aforementioned transmission grounding wire and reception grounding wire are integrated as a common grounding wire, and the aforementioned common grounding wire and transmission signal wire, and the common grounding wire and reception signal wire are arranged on different side surfaces from each other of the mutually superposed transmission section and reception section.

In the aforementioned arrangement, the transmission grounding wire and reception grounding wire are integrated as a common grounding wire. This reduces the number of wires, and hence, increases the space between wires, as compared to the case where the grounding wire for transmission and the grounding wire for reception are separately installed from each other. The common grounding wire and transmission signal wire, and the common grounding wire and reception signal wires are arranged on different side surfaces from each other of the mutually superposed transmission and reception sections. Further, the reception and transmission sections are mutually superposed and the wires are located at different positions on the upper and lower sides. Thus, the reception and transmission sections are located far from each other, with the result that cross talk can be minimized.

In the present invention, the side surface is different from the transmission and reception surfaces of the ultrasonic wave in the mutually superposed transmission and reception sections, includes one of the edges of both ends, and one edge is included in two adjacent side surfaces wherein the former edge serves as a boundary.

In the aforementioned ultrasonic transmitter/receiver device, the common grounding wire is arranged on the edge wherein two side surfaces are adjacent to each other in the mutually superposed transmission and reception sections.

In the aforementioned ultrasonic transmitter/receiver device, the aforementioned transmission signal wire is arranged on the edge where two side surfaces are adjacent to each other in the mutually superposed transmission and reception sections.

According to this structure, the transmission signal wire is arranged on the edge of the side surface. This allows the transmission signal wire and reception signal wire to be placed far from each other. This arrangement further reduces cross talk.

In the ultrasonic transmitter/receiver device of another embodiment, the reception signal wire is arranged on the edge wherein two side surfaces are adjacent to each other in the mutually superposed transmission and reception sections.

According to this structure, the reception signal wire is arranged on the edge of the side surface. This allows the transmission signal wire and reception signal wire to be placed far from each other. This arrangement further reduces cross talk.

In the aforementioned ultrasonic transmitter/receiver device, the piezoelectric element of the reception section is formed of an organic piezoelectric material.

According to this structure, the piezoelectric element of the reception section is formed of an organic piezoelectric material capable of receiving the ultrasonic wave over a wide frequency range. This ensures the frequency to be increased in bandwidth using a comparatively simple structure, with the result that the ultrasonic wave ranging from the frequency of a fundamental wave to the frequency of a harmonic wave thereof can be received.

The ultrasonic probe of still another embodiment of the present invention is provided with a plurality of any one of the desired ultrasonic transmitter/receiver devices described above.

This structure provides an ultrasonic probe provided with ultrasonic transmitter/receiver devices characterized by minimized cross talk.

The ultrasonic diagnostic apparatus of a further embodiment of the present invention is provided with the aforementioned ultrasonic probe.

The aforementioned structure provides an ultrasonic diagnostic apparatus provided with an ultrasonic probe characterized by minimized cross talk.

EFFECTS OF THE INVENTION

The ultrasonic transmitter/receiver device of the present invention is characterized by minimized crass talk. The present invention provides the ultrasonic probe and ultrasonic diagnostic apparatus provided with such an ultrasonic transmitter/receiver device.

BRIEF DESCRIPTION OF THE DRAWINGS

FIGS. 7a-7g are diagrams representing the second through ninth examples of the reception and transmission signal wires and a common grounding wire in the ultrasonic transmitter/receiver device.

DESCRIPTION OF REFERENCE NUMERALS

Figure 1:
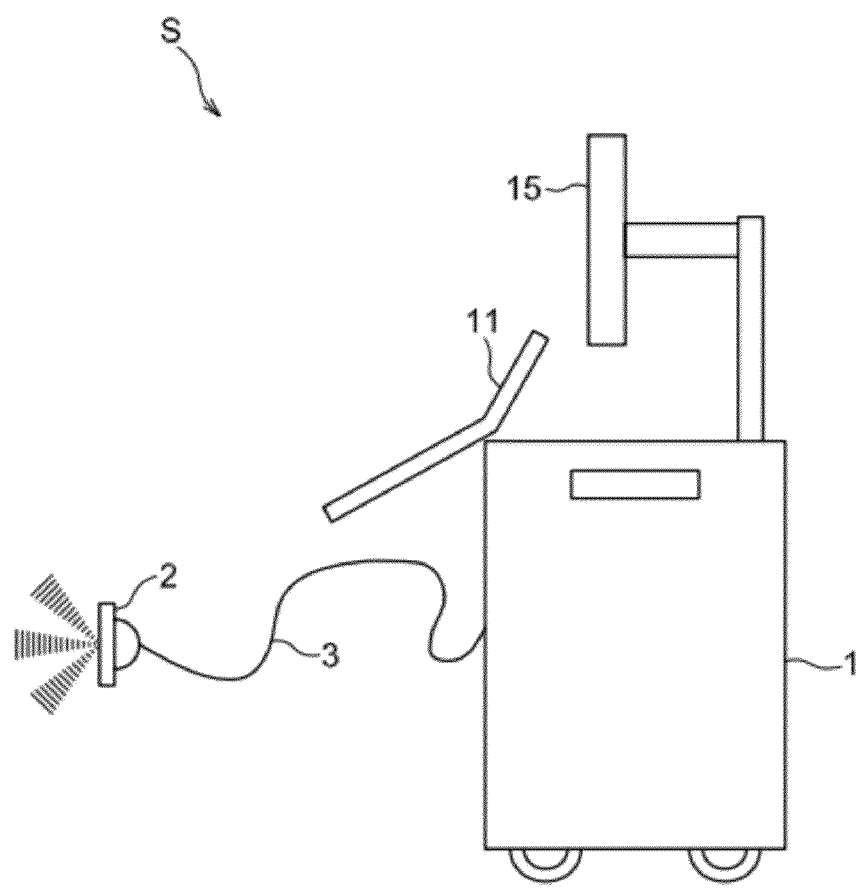
FIG. 1 is a diagram representing the external structure of the ultrasonic diagnostic apparatus of an embodiment of the present invention.

S. Ultrasonic diagnostic apparatus
1. Ultrasonic diagnostic apparatus body
2. Ultrasonic probe
11. Operation input section 12. Transmitting circuit
13. Receiving circuit
14. Image processing section
15. Display section
16. Control section
21. Ultrasonic transmitter/receiver device
21a-21d. Side surfaces
32. Transmission section
32-1, 32-2, 32-3. Piezoelectric element
34. Reception section
34-1, 34-2, 34-3. Piezoelectric element
37. Reception signal wire
38. Transmission signal wire
39. Common grounding wire
d. Outgoing wire

DETAILED DESCRIPTION OF THE PREFERRED
EMBODIMENTS

Figure 2:
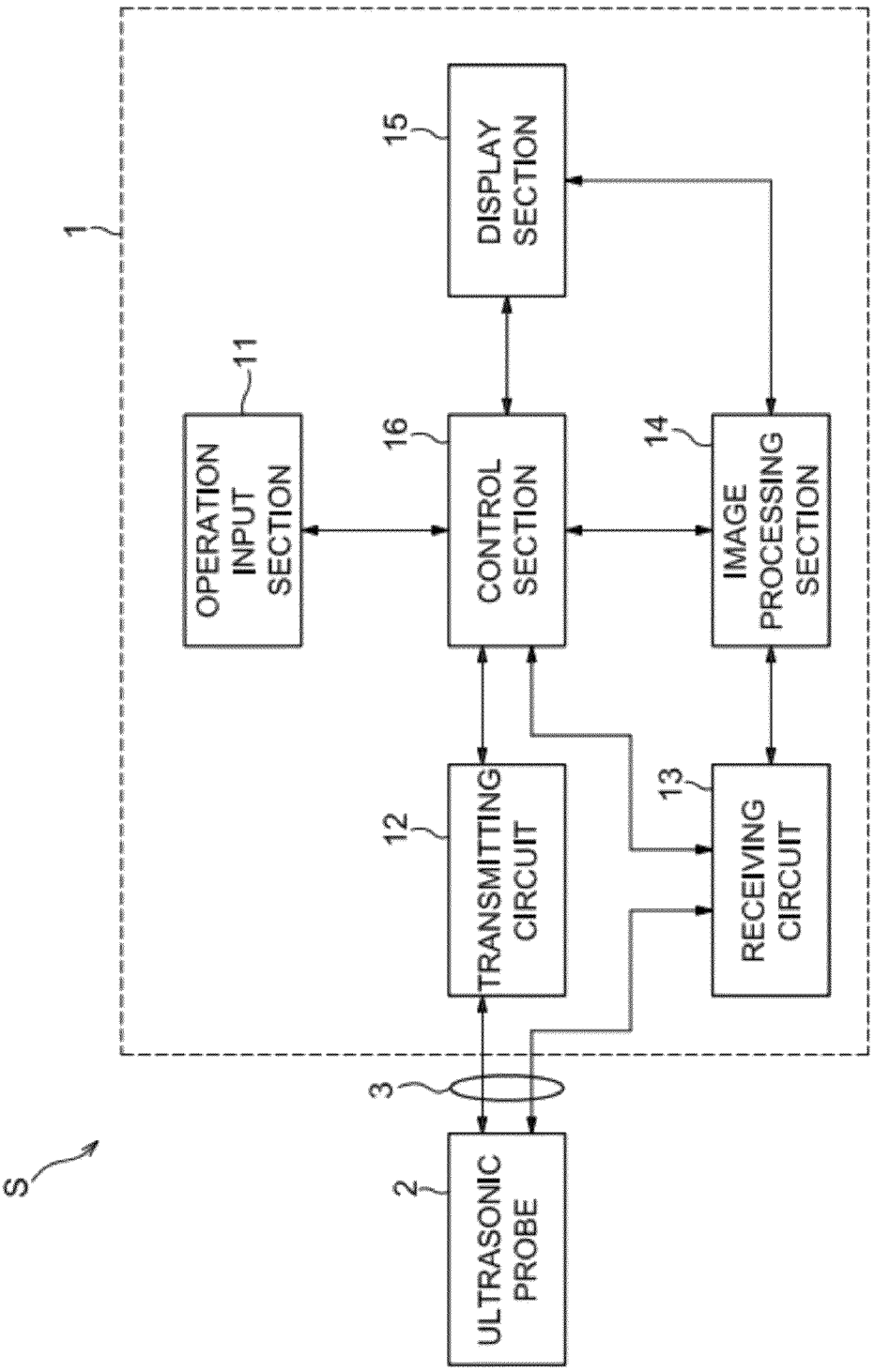
FIG. 2 is a block diagram representing the electric structure of the ultrasonic diagnostic apparatus of an embodiment of the present invention.
Figure 3:
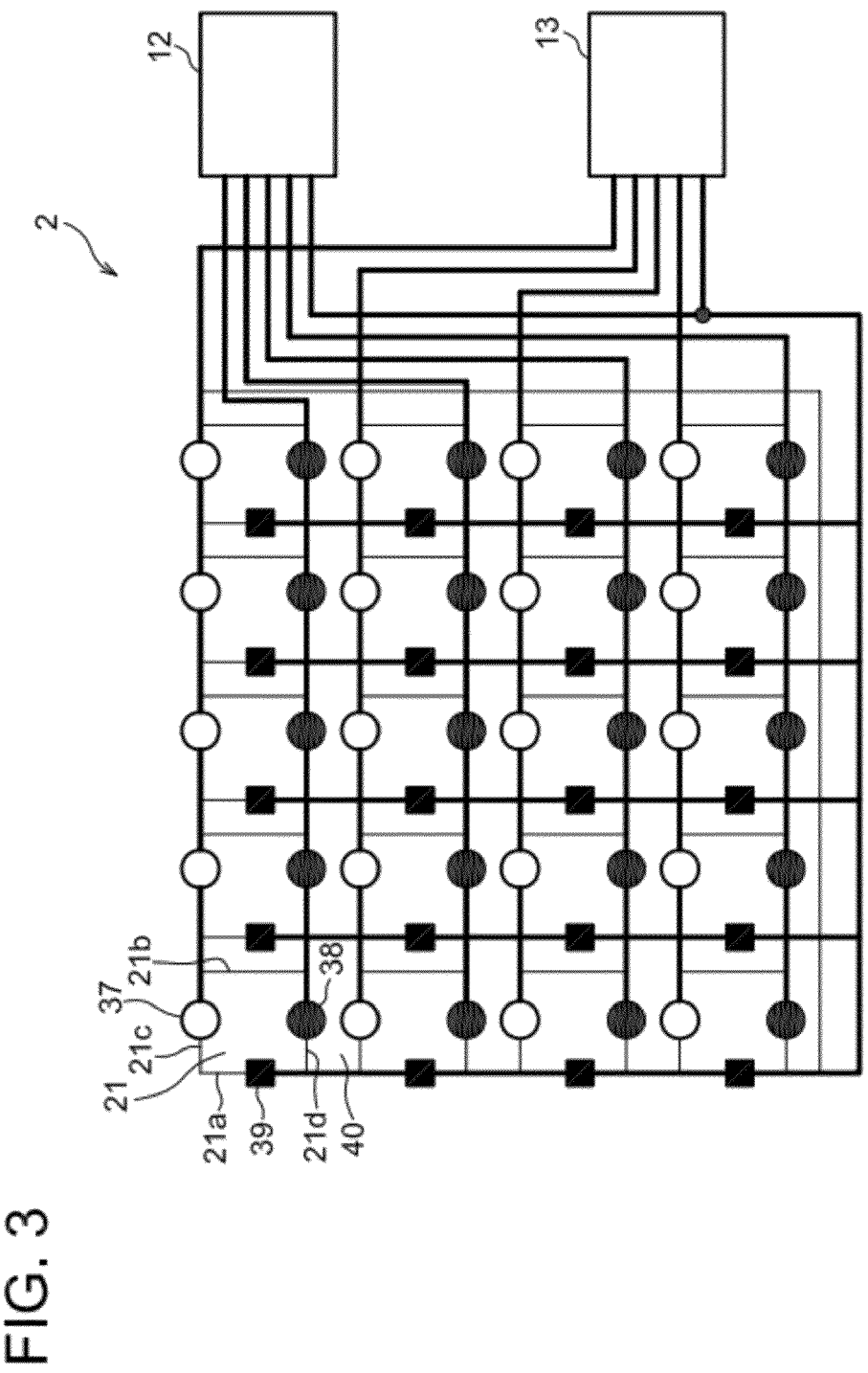
FIG. 3 is a plan view representing the ultrasonic probe in the ultrasonic diagnostic apparatus of an embodiment of the present invention.
Figure 4:
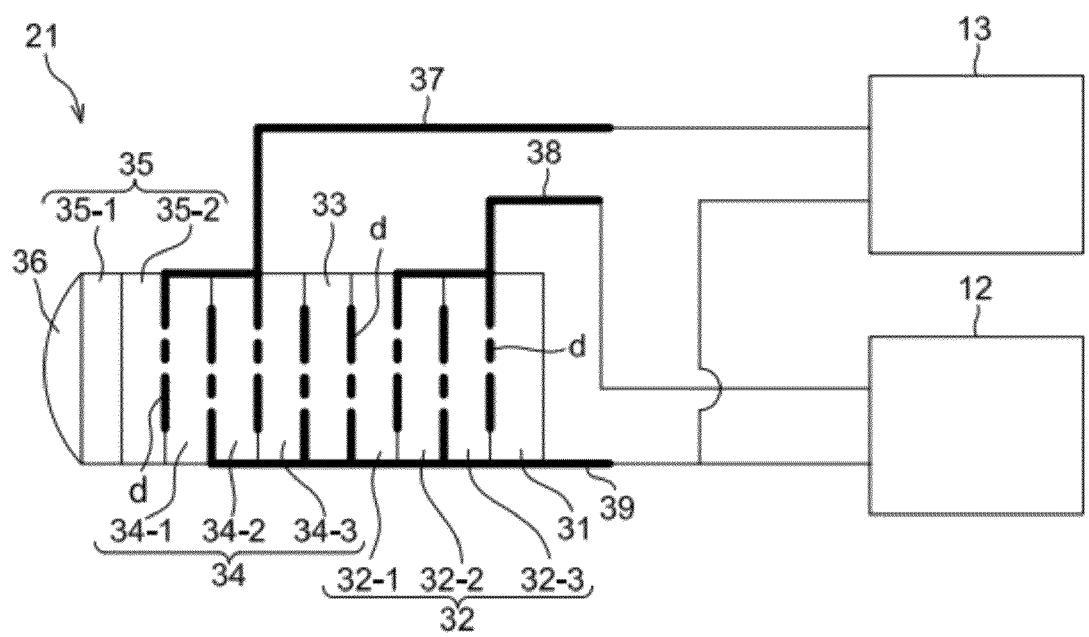
FIG. 4 is a cross sectional view of the ultrasonic transmitter/receiver device in the ultrasonic probe of the ultrasonic diagnostic apparatus of an embodiment of the present invention.

The following describes an embodiment of the present invention with reference to the drawings. The same portions in the drawings will be assigned with the same reference numerals, and will not be described to avoid duplication.
(Configurations of Embodiments)
FIG. 1 is a diagram representing the external structure of the ultrasonic diagnostic apparatus of an embodiment of the present invention. FIG. 2 is a block diagram representing the electric structure of the ultrasonic diagnostic apparatus of an embodiment of the present invention. FIG. 3 is a plan view representing the ultrasonic probe in the ultrasonic diagnostic apparatus of an embodiment of the present invention. FIG. 4 is a cross sectional view of the ultrasonic transmitter/receiver device in the ultrasonic probe of the ultrasonic diagnostic apparatus of an embodiment of the present invention.

As shown in FIGS. 1 and 2, the ultrasonic diagnostic apparatus S includes an ultrasonic probe 2 for transmitting the ultrasonic wave to the test object such as a living body not shown in the sketch, and for receiving the echo of the ultrasonic wave reflected by the test object, and an ultrasonic diagnostic apparatus body 1 which is connected to the ultrasonic probe 2 via cable 3 to transmit the transmission signal of electric signal to the ultrasonic probe 2 via cable 3, whereby the ultrasonic probe 2 is allowed to send the ultrasonic wave to the test object, and an image of the internal state of the test object is formed based on the reception signal of electric signal generated by the ultrasonic probe 2 in response to the reflected wave of the ultrasonic wave coming from inside the test object and received by the ultrasonic probe 2.

As shown in FIG. 2, for example, the ultrasonic diagnostic apparatus body 1 includes an operation input section 11 for inputting such data as the command instructing the start of diagnosis and the personal information on the test object, a transmitting circuit 12 that supplies the transmission signal of electric signal to the ultrasonic probe 2 through the cable 3 so that the ultrasonic wave is generated by the ultrasonic probe 2, a receiving circuit 13 for receiving the reception signal of electric signal through the cable 3 from the ultrasonic probe 2, an image processing section 14 for generating an image of the internal state of the test object based on the reception signal received by the receiving circuit 13, a display section 15 for displaying the image of the internal state of the test object generated by the image processing section 14, and a control section 16 that provides the overall control of the ultrasonic diagnostic apparatus S by controlling the operation input section 11, transmitting circuit 12, receiving circuit 13, image processing section 14 and display section 15 in response to the relevant functions.

The ultrasonic probe 2 includes a plurality of ultrasonic transmitter/receiver devices for transmission and reception of the ultrasonic wave. As shown in FIG. 3, for example, the input/output surface for inputting and outputting the ultrasonic wave to and from the test object is configured so that a plurality of ultrasonic transmitter/receiver devices 21 are arranged in a two-dimensional array with "m" rows and "n" columns in two linear and independent directions at right angles (two mutually intersecting directions in the example of FIG. 3) (wherein "m" and "n" are positive integers). The ultrasonic transmitter/receiver devices 21 are arranged at predetermined intervals (gap, groove) for the purpose of acoustic separation. The aforementioned interval is filled with the acoustic absorbent 40 made of resin or other materials which absorbs ultrasonic wave. This acoustic absorbent 40 in this embodiment also serves as an electric insulating material, since a reception signal wire 37, transmission signal wire 38 and common grounding wire 39 are arranged on the side surface of the ultrasonic transmitter/receiver device 21, as will be described later. From the viewpoint of ensuring the insulating performances, the acoustic absorbent 40 is made of a thermosetting resin such as polyimide resin and epoxy resin, for example.

In the present embodiment, an example of the two-dimensional array oscillator is used to illustrate the ultrasonic probe 2. However, the ultrasonic probe 2 can also be made of a line oscillator wherein a plurality of ultrasonic transmitter/receiver devices is arranged in a straight line. The ultrasonic probe 2 can be used in contact with the surface of the test object. It can also be used by being inserted in the test object, for example, in the body cavity of a test object.

As shown in FIG. 4, for example, the ultrasonic transmitter/receiver device 21 includes a sound absorbing layer 31 provided on the wiring board not illustrated toward the test object, a transmission section 32 (piezoelectric elements 32-1 through 32-3) provided on the sound absorbing layer 31, a buffer layer 33 provided on the transmission section 32, a reception section 34 (piezoelectric elements 34-1 through 34-3) provided on the buffer layer 33, an acoustic matching layer 35 (35-1 and 35-2) provided on the reception section 34, and an acoustic lens 36 provided on the acoustic matching layer 35, and reception signal wire 37, transmission signal wire 38 and common grounding wire 39. "d" indicates an outgoing wire used for connection between the transmission section 32 and transmission signal wire 38, between the reception section 34 and reception signal wire 37, and between the transmission section 32 (or reception section 34) and common grounding wire 39. In this embodiment, the outgoing wire "d" extends across the superposed layers (in the direction of plane surface). The reception signal wire 37, transmission signal wire 38 and common grounding wire 39 serve as an intermediary between superposed layers, and extend in the direction of the superposition of layers (along the height).

In the present specification, a reference letter without an attached letter is used for collective indication, and a reference letter with an attached letter is used for indication of an individual structure.

The sound absorbing layer 31 (acoustic damping layer) is a member that damps and absorbs the ultrasonic wave generated by the transmission section 32 and propagated in the direction of the sound absorbing layer 31 to ensure that this ultrasonic wave will not return to the transmission section 32. Further, the sound absorbing layer 31 damps and absorbs the ultrasonic wave components at the time of reception that are not required for image formation.

When the electric transmission signal has been inputted, the transmission section 32 transmits the ultrasonic wave generated by the piezoelectric element. The transmission section 32 includes one or more piezoelectric elements. In the present embodiment, the transmission section 32 contains three first through third piezoelectric elements 32-1 through 32-3 and configured with the first through third piezoelectric elements 32-1 through 32-3 superposed. Use of such a multilayer structure increases the transmission output (transmission power) over that of a single layer structure. The first through third piezoelectric elements 32-1 through 32-3 are made of such inorganic piezoelectric materials as PZT (lead zirconate titanate), lithium niobate, barium titanate, and lead titanate. The piezoelectric element made of inorganic piezoelectric material is characterized by a greater transmission power than the piezoelectric element made of organic, piezoelectric material.

Electrode layers are provided on both sides of the first through third piezoelectric elements 32-1 through 32-3. The electrode layer provided on one side of the first piezoelectric element 32-1 (the electrode layer sandwiched by the buffer layer 33 and first piezoelectric element 32-1) is used as a grounding electrode layer, and is connected to the common grounding wire 39 that serves as a grounding wire for transmission through the outgoing wire "d" arranged on the side surface. The electrode layer arranged on the other side of the first piezoelectric element 32-1 (electrode layer sandwiched by the first piezoelectric element 32-1 and second piezoelectric element 32-2) is connected to the transmission signal wire 38 through the outgoing wire "d" provided on the side surface. In this electrode layer arranged on the other side of the first piezoelectric element 32-1, the first and second piezoelectric elements 32-1 and 32-2 are mutually superposed. Accordingly, this electrode layer is jointly used by the first piezoelectric element 32-1 and second piezoelectric element 32-2, and also serves as an electrode layer arranged on one side of the second piezoelectric element 32-2. The electrode layer arranged on the other side of the second piezoelectric element 32-2 (electrode layer sandwiched by the second piezoelectric element 32-2 and third piezoelectric element 32-3) is connected to the common grounding wire 39 through the outgoing wire "d" arranged on the side surface. In this electrode layer arranged on the other side of the second piezoelectric element 32-2, the second and third piezoelectric element 32-2, 32-3 are mutually superposed. Accordingly, this layer is jointly used by the second piezoelectric element 32-2 and third piezoelectric element 32-3, and also serves as an electrode layer arranged on one side of the third piezoelectric element 32-3. The electrode layer arranged on the other side of the third piezoelectric element 32-3 (electrode layer sandwiched by the third piezoelectric element 32-3 and sound absorbing layer 31) is connected to the transmission signal wire 38 through the outgoing wire "d" located on the side surface. A set of the transmission signal wire 38 and common grounding wire 39 is connected to the transmitting circuit 12 through the cable 3.

When the voltage based on the transmission signal supplied by a set of transmission signal wire 38 and common grounding wire (grounding wire for transmission) 39 has been applied to a pair of electrode layers arranged on one and the other sides of each of the first through third piezoelectric elements 32-1 through 32-3, the electric transmission signal is converted into mechanical vibration by the occurrence of piezoelectric phenomenon. This ensures that the transmission section 32 sends an ultrasonic wave toward the test object.

In the present embodiment, the transmission section 32 is provided with three layers such as first through third piezoelectric elements 32-1 through 32-3. However, the transmission section 32 can be provided with one layer or layers of other number, for example, two, four, five, ten and twenty layers.

The buffer layer 33 is a member for superposing the transmission section 32 and reception section 34, and is used to match the acoustic impedances of the transmission section 32 and the reception section 34.

The reception section 34 is laid on the transmission section 32 through the buffer layer 33, and is used to output the electric reception signal generated by the piezoelectric element when the ultrasonic wave has been received. The reception section 34 is equipped with one or more than one piezoelectric element. The present embodiment includes three first through third piezoelectric elements 34-1 through 34-3. These first through third piezoelectric elements 34-1 through 34-3 are superposed to constitute the reception section 34. Use of such a multilayer structure increases the reception sensitivity over that of a single layer structure. The first through third piezoelectric elements 34-1 through 34-3 are made of organic piezoelectric materials such as vinylidene polyfluoride and polyurea in order to ensure reception of a wide frequency band ranging from the frequency of the fundamental wave to the frequency of the harmonic wave in a comparatively simple structure. Generally, the piezoelectric element of inorganic piezoelectric material is capable of receiving only the ultrasonic wave having the frequency about twice that of the fundamental wave. However, the piezoelectric element made of organic piezoelectric material is capable of receiving the ultrasonic wave having the frequency about four or five times that of the fundamental wave, for example. Thus, the piezoelectric element made of organic piezoelectric material can be effectively used to increase the bandwidth of the received frequency. To expand the frequency band for reception, the reception section 34 can be made of the piezoelectric element of inorganic piezoelectric material by adopting the structure for expanded bandwidth, wherein a plurality of piezoelectric elements having different thicknesses are used, for example. In this case, the number of layers and the number of wires are increased as compared to the case wherein the organic piezoelectric material is used. For this reason, the piezoelectric element made of organic piezoelectric material is preferably used to constitute the reception section 34.

Electrode layers are provided on both sides of each of the first through third piezoelectric elements 34-1 through 34-3. The electrode layer provided on one side of the first piezoelectric element 34-1 (electrode layer sandwiched between the acoustic matching layer 35 and first piezoelectric element 34-1) is connected to the reception signal wire 37 through the outgoing wire "d" provided on the side surface. The electrode layer arranged on the other side of the first piezoelectric element 34-1 (electrode layer sandwiched by the first piezoelectric element 34-1 and second piezoelectric element 34-2) is used as a grounding electrode layer, and is connected to the common grounding wire 39 serving as the reception grounding wire through the outgoing wire "d" located on the side surface. In this electrode layer arranged on the other side of the first piezoelectric element 34-1, the first piezoelectric element 34-1 and second piezoelectric element 34-2 are mutually superposed. Accordingly, this electrode layer is jointly used by the first piezoelectric element 34-1 and second piezoelectric element 34-2, and also serves as the electrode layer arranged on one side of the second piezoelectric element 34-2. The electrode layer arranged on the other side of the second piezoelectric element 34-2 (electrode layer sandwiched by the second piezoelectric element 34-2 and third piezoelectric element 34-3) is connected to the reception signal wire 37 through the outgoing wire "d" located on the side surface. In this electrode layer arranged on the other side of the second piezoelectric element 34-2, the second and the third piezoelectric elements 34-2. 34-3 are mutually superposed. Accordingly, this electrode layer is jointly used by the second piezoelectric element 34-2 and third piezoelectric element 34-3, and also serves as the electrode layer arranged on one side of the third piezoelectric element 34-3. The electrode layer arranged on the other side of the third piezoelectric element 34-3 (electrode layer sandwiched by the third piezoelectric element 34-3 and buffer layer 33) is connected to the common grounding wire 39 through the outgoing wire "d" located on the side surface. A set of the reception signal wire 37 and common grounding wire 39 is connected to the receiving circuit 13 through the cable 3.

The ultrasonic wave transmitted to the test object is reflected by one or more boundary surfaces having different acoustic impedances inside the test object, and is turned into the reflected wave of the ultrasonic wave. This reflected wave of the ultrasonic wave is received by the reception section 34, and the mechanical vibration is converted into the electric signal by the first through third piezoelectric elements 34-1 through 34-3. This signal is picked up as the reception signal from a pair of electrode layers arranged respectively on one side and on the other side of each of the first through third piezoelectric elements 34-1 through 34-3, by a pair of the reception signal wire 37 and common grounding wire 39 (grounding wire for reception). Thus, the reception section 34 receives the ultrasonic wave from the test object.

In the present invention, the reception section 34 is made up of the first through third piezoelectric elements 34-1 through 34-3 in three layers. However, the reception section 34 can be provided with one layer or layers of other number, for example, two, four, five, ten and twenty layers. Further, in the present embodiment, the number of the piezoelectric element layers in the transmission section 32 is three, and the number of the piezoelectric element layers in the reception section 34 is also three. However, the number of layers can be different. The number of the piezoelectric element layers in the transmission section 32 can be greater than that of the piezoelectric element layers in the reception section 34, and vice versa. Further, in the present invention, the reception section 34 is laid indirectly through the buffer layer 33 on the transmission section 32, but can also be laid on directly. In the present embodiment, to enhance the sensitivity of reception, the reception section 34 is provided toward the test object on the transmission section 32 through the buffer layer 33. However, the transmission section 32 can be provided toward the test object on the reception section 34 through the buffer layer 33.

The acoustic matching layer 35 is a member for matching the acoustic impedances of the transmission section 32 and the test object. The acoustic matching layer 35 is also used to match the acoustic impedances of the reception section 34 and the test object. In the present embodiment, the acoustic matching layer 35 is made up of the first and second acoustic matching layer 35-1, 35-2 in two layers, for example. To expand the reception frequency bandwidth, the number of layers of the acoustic matching layer 35 can be further increased.

The acoustic lens 36 converges the ultrasonic wave transmitted from the transmission section 32 toward the test object, and is formed in such a way as to protrude in a circular arc, for example, as shown in FIG. 4.

The transmission signal wire 38 forms a set in combination with the grounding wire for transmission to supply the transmission signal to the transmission section 32. The reception signal wire 37 forms a set in combination with the grounding wire for reception to pick up the reception signal from the reception section 34.

It should be noted that, in this embodiment, the grounding wire for transmission and the grounding wire for reception are integrated into the common grounding wire 39 for common use. This arrangement reduces the number of the wires, and increases the wiring interval as compared with the case where the grounding wire for transmission is separate from the grounding wire for reception. It should also be noted that, in the present embodiment, the common grounding wire 39 and transmission signal wire 38, and common grounding wire 39 and reception signal wire 37 are arranged on different side surfaces from each other in the transmission section 32 and reception section 34 superposed. In this arrangement, the transmission section 32 and reception section 34 are mutually superposed and the reception signal wire 37 and transmission signal wire 38 are located at different positions on the upper and lower sides. Thus, the reception and transmission signal wires are located far from each other, with the result that cross talk can be minimized.

The reception signal wire 37, transmission signal wire 38 and common grounding wire 39 can be made of such a lead wire as a bonding wire to ensure that these wires are located apart from the side surface. Further, these wires can be made of a linear conductive film having a predetermined width so that these wires are bonded to the side surface. Such a conductive film can be formed by vapor deposition or electroless plating method, for example.

In the ultrasonic diagnostic apparatus S having such a structure, for example, when an instruction to start diagnosis has been inputted from the operation input section 11, an electric transmission signal is generated by the transmitting circuit 12 under the control of the control section 16. The electric transmission signal having been generated is supplied to the ultrasonic probe 2 through the cable 3. To put it more specifically, this transmission signal is supplied to the transmission section 32 by the transmission signal wire 38 and common grounding wire 39 on the ultrasonic transmitter/receiver device 21 of the ultrasonic probe 2. The transmission signal is the voltage pulse repeated on a predetermined cycle, for example. The first through third piezoelectric elements 32 of the transmission section 32 expand and contract along the thickness when this electric transmission signal has been supplied. Ultrasonic oscillation is caused in response to this transmission signal, and the ultrasonic wave is emitted through the buffer layer 33, reception section 34, acoustic matching layer 35 and acoustic lens 36. When the ultrasonic probe 2 is brought in contact with the test object, the ultrasonic wave is sent to the test object from the ultrasonic probe 2.

The ultrasonic wave transmitted to the test object is reflected by one or more boundary surfaces having different acoustic impedances inside the test object, and is turned into a reflected ultrasonic wave. This reflected wave includes not only the frequency component having been transmitted (the component of the fundamental frequency of the fundamental wave), but also the frequency component of the harmonic equivalent to an integral multiple of the fundamental frequency. For example, the reflected wave also includes the second, third and fourth harmonic components which are two times, three times and four times the fundamental frequency. This reflected ultrasonic wave is received by the ultrasonic probe 2. To put it more specifically, this reflected ultrasonic wave is received by the reception section 34 through the acoustic lens 36 and acoustic matching layer 35. The mechanical vibration is converted into the electric signal by the first through third piezoelectric elements 34-1 through 34-3. This ultrasonic wave is picked up as the reception signal by a set of the reception signal wire 37 and common grounding wire 39 from a pair of electrode layers arranged in one and the other sides of each of the first through third piezoelectric elements 34-1 through 34-3. The electric reception signal having been picked up is received through the cable 3 by the receiving circuit 13 under the control of the control section 16.

In the above description, the ultrasonic wave is transmitted successively toward the test object from the ultrasonic transmitter/receiver device 21. The ultrasonic wave reflected by the test object is received by one or more ultrasonic transmitter/receiver devices 21.

The image processing section 14 generates an image of the internal state of the test object under the control of the control section 16 according to the time required from transmission to reception and the intensity of reception, based on the signal received by the receiving circuit 13. The display section 15 displays the image of the internal state of the test object generated in the image processing section 14, under the control of the control section 16.

The ultrasonic diagnostic apparatus S, ultrasonic probe 2 and ultrasonic transmitter/receiver device 21 of the present embodiment operate as described above. The grounding wire for transmission and grounding wire for reception are integrated as the common grounding wire 39 for common use. The common grounding wire 39 and transmission signal wire 38, and the common grounding wire 39 and reception signal wire 37 are arranged on mutually different side surfaces in the transmission section 32 and reception section 34 superposed. This arrangement reduces the number of wires, and therefore, expands the wiring interval over that in the case wherein the grounding wire for transmission is separate from the grounding wire for reception. Further, the transmission section 32 and reception section 34 are laid on each other and the reception signal wire 37 and transmission signal wire 38 are located at different positions on the upper and lower sides. Thus, the reception signal wire 37 and transmission signal wire 38 are located far from each other, with the result that cross talk between wires can be minimized in the ultrasonic diagnostic apparatus S, ultrasonic probe 2 and ultrasonic transmitter/receiver device 21 of the present embodiment.

Further, the minimized cross talk between wires enhances the sensitivity of the ultrasonic probe 2 and ultrasonic transmitter/receiver device 21 in the ultrasonic diagnostic apparatus S, ultrasonic probe 2 and ultrasonic transmitter/receiver device 21 of the present embodiment, and expands the dynamic range. Such improvements upgrade the performance of the apparatus.

The following will give a more specific description of the reception signal wire 37, transmission signal wire 38 and common grounding wire 39 arranged on the side surface of the mutually superposed transmission section 32 and reception section 34.

Figure 5A:
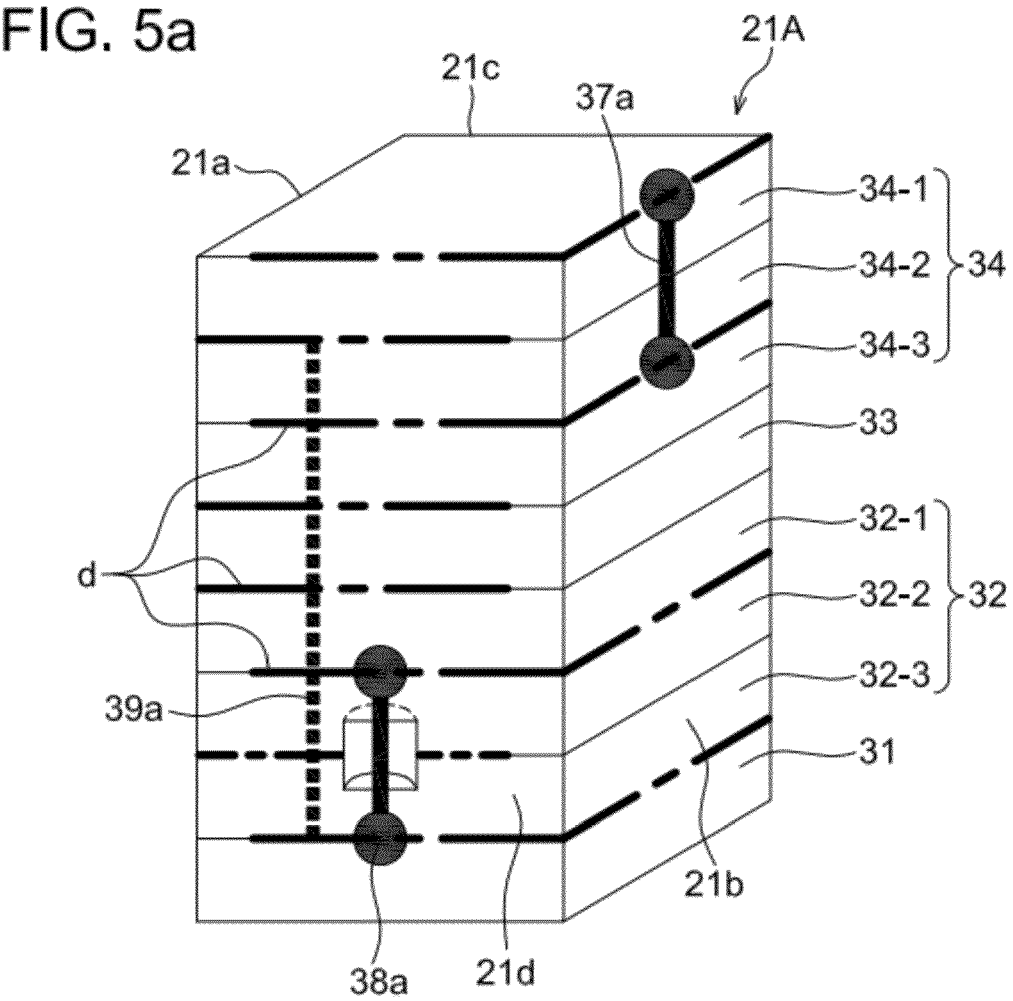
FIGS. 5a and 5b are diagrams representing the first example of the reception and transmission signal wires and common grounding wire in the ultrasonic transmitter/receiver device.
Figure 5B:
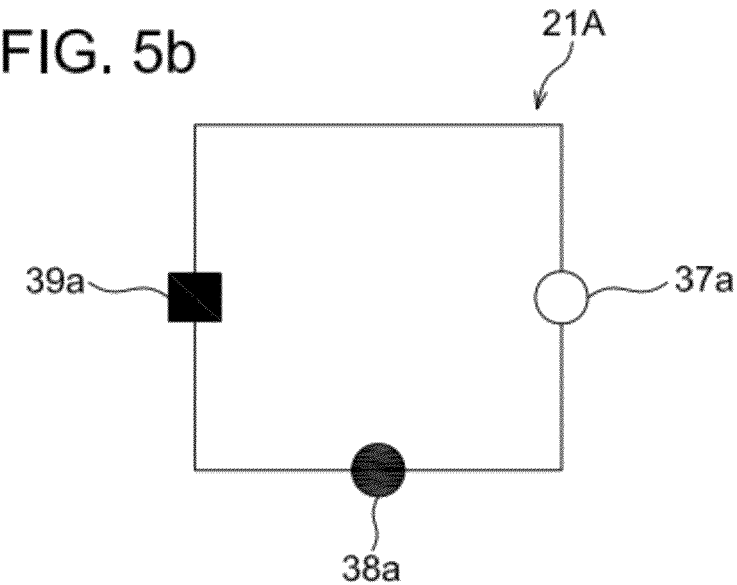
Figure 6A:
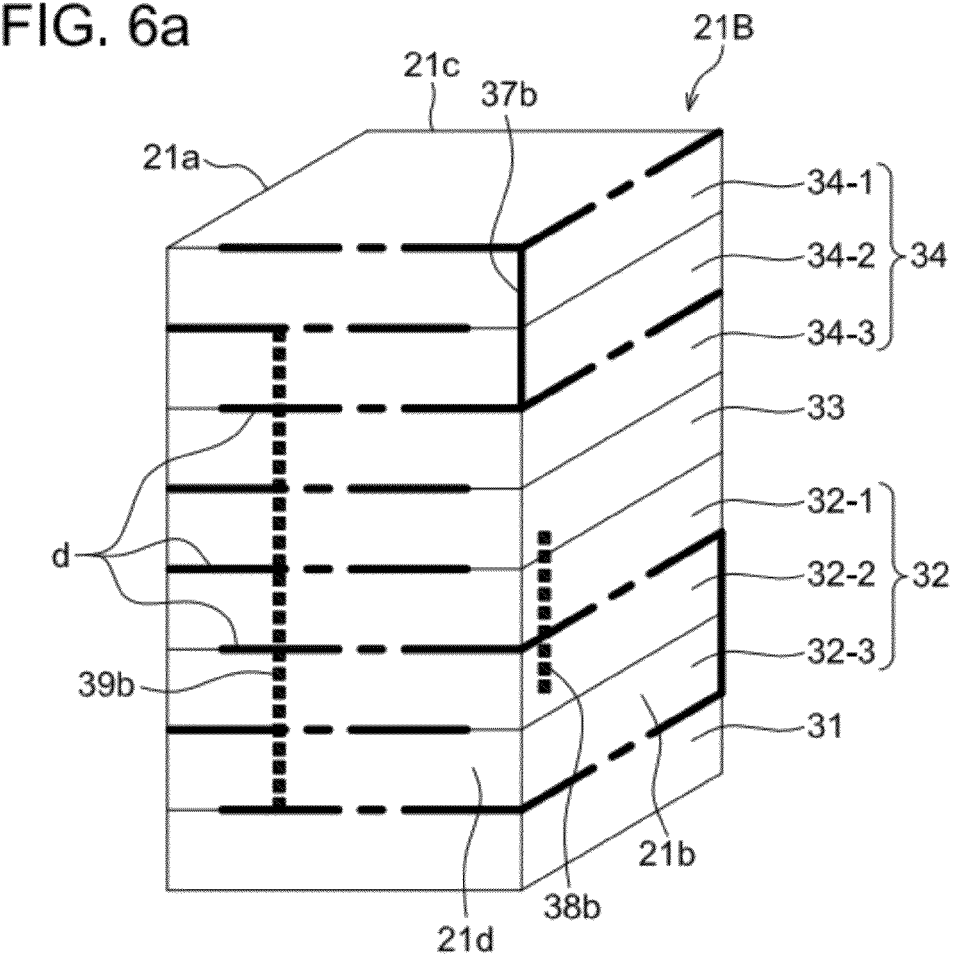
FIGS. 6a and 6b are diagrams representing the second example of the reception and transmission signal wires and common grounding wire in the ultrasonic transmitter/receiver device.
Figure 6B:
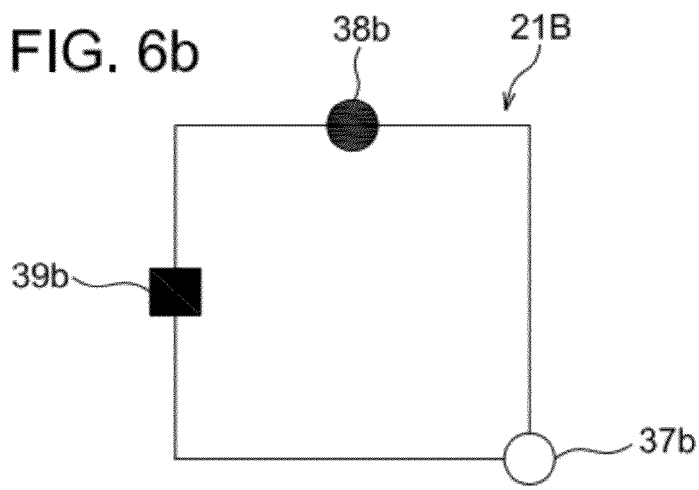
Figure 8:
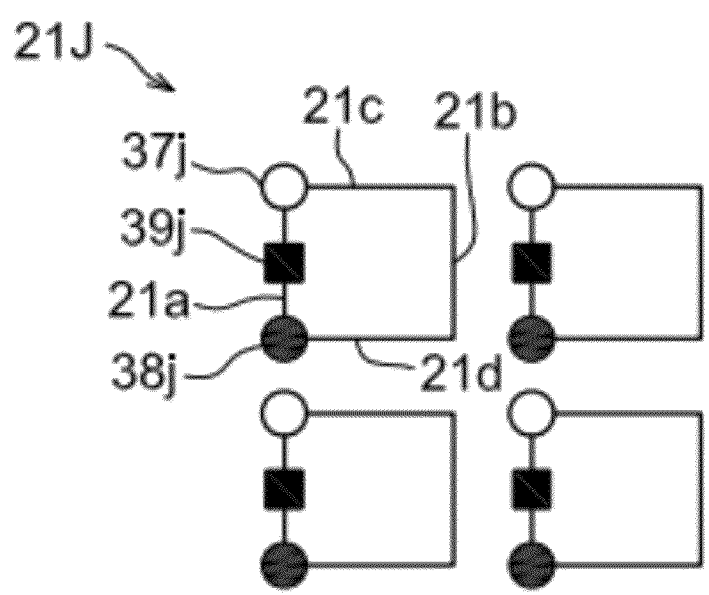
FIG. 8 is a diagram representing a comparative example of the reception and transmission signal wires and common grounding wire in the ultrasonic transmitter/receiver device.

FIGS. 5a and 5b are diagrams representing the first example of the reception and transmission signal wires and common grounding wire in the ultrasonic transmitter/receiver device. FIGS. 6a and 6b are diagrams representing the second example of the reception and transmission signal wires and a common grounding wire in the ultrasonic transmitter/receiver device. FIG. 5a and FIG. 6a are the perspective views of the ultrasonic transmitter/receiver device. FIG. 5b and FIG. 6b are the plan views when viewed from the input/output surface of the ultrasonic wave. FIGS. 7a-7g are diagrams representing the third through ninth examples of the reception and transmission signal wires and common grounding wire in the ultrasonic transmitter/receiver device. Each of FIGS. 7a-7g shows a plan view viewed from the input/output surface, that represents a two by two, four ultrasonic transmitter/receiver devices 21 among a plurality of those arranged in the ultrasonic probe 2. FIG. 8 is a diagram representing a comparative example of the reception and transmission signal wires and common grounding wire in the ultrasonic transmitter/receiver device.

As shown in FIGS. 5a and 5b, the ultrasonic transmitter/receiver device 21A of the first example is designed in the form of a quadrangular prism, and includes a rectangular emission/entry surface for emission and entry of the ultrasonic wave, and four first through fourth side surfaces 21a, 21b, 21c and 21d perpendicular to this emission/entry surface. The common grounding wire 39a is arranged approximately at the center of the first side surface 21a in the superposition direction of the reception section 34 and transmission section 32. To be more specific, the common grounding wire 39a is mounted along the superposition at a position approximately equidistant from the edges on both ends of the first side surface 21a. The reception signal wire 37a is arranged on the second side surface 21b opposed to the first side surface 21a. The transmission signal wire 38a is located on the fourth side surface 21d. The transmission signal wire 38a and reception signal wire 37a are also located approximately at the centers of the respective side surfaces (at positions equidistant from the edges on both ends of each side surface).

The ultrasonic transmitter/receiver device 21B of the second example is approximately the same as the ultrasonic transmitter/receiver device 21A of the first example. The difference is that the reception signal wire 37b is positioned at the edge on the boundary between the second side surface 21b and fourth side surface 21d, as shown in FIGS. 6a and 6b. The ultrasonic transmitter/receiver device 21B of the second example is constructed in such a way that the common grounding wire 39b, transmission signal wire 38b and reception signal wire 37b are arranged on two mutually different side surfaces in the mutually superposed transmission section 32 and reception section 34. Further, the reception signal wire 37b is arranged on the edge where two side surfaces are adjacent to each other in the mutually superposed transmission section and reception section.

The ultrasonic transmitter/receiver device 21C of the third example is approximately the same as the ultrasonic transmitter/receiver device 21A of the first example. As shown in FIG. 7a, the difference is that the reception signal wire 37c is arranged on the side surface sandwiched between the first side surface 21a and second side surface 21b, not on the second side surface 21b. In other words, the reception signal wire 37c is located on the fourth side surface 21d in the example of FIG. 7a. In the example of FIG. 7a, the reception signal wire 37c is located in the superposition direction approximately at the center of the fourth side surface 21d (at a position equidistant from the edges on both ends of the fourth side surface 21d). In the example of FIG. 7a, the transmission signal wire 38c is located in the superposition direction approximately at the center of the second side surface 21b (at a position equidistant from the edges on both ends of the second side surface 21b).

The ultrasonic transmitter/receiver device 21D of the fourth example is approximately the same as the ultrasonic transmitter/receiver device 21A of the first example. As shown in FIG. 7b, one of the differences is that the transmission signal wire 38d is arranged on the side surface sandwiched between the first side surface 21a and second side surface 21*b*, not on the second side surface 21*b*. In other words, the transmission signal wire 38*d* is located on the fourth side surface 21*d* in the example of FIG. 7*b*. Another difference is that the reception signal wire 37*d* is arranged on the side surface sandwiched between the first side surface 21*a* and second side surface 21*b*, not on the second side surface 21*b*. In other words, in the example of FIG. 7*b*, the reception signal wire 37*d* is located on the third side surface 21*c*. To be more specific, the transmission signal wire 38*d* and reception signal wire 37*d* are arranged on the mutually opposed third and fourth side surfaces 21*c* and 21*d*, respectively, with these side surfaces being different from the first side surface 21*a* where the common grounding wire 39*d* is mounted. In the example of FIG. 7*b*, the transmission signal wire 38*d* is located along the superposition approximately at the center of the fourth side surface 21*d* (at a position approximately equidistant from the edges on both ends of the fourth side surface 21*d*). In the example of FIG. 7*b*, the reception signal wire 37*d* is arranged along the superposition approximately at the center of the third side surface 21*c* (at a position approximately equidistant from the edges on both ends of the third side surface 21*c*).

FIG. 3 shows one example of the ultrasonic probe 2 equipped with the ultrasonic transmitter/receiver device 21D of the fourth example.

The ultrasonic transmitter/receiver device 21E of the fifth example is approximately the same as the ultrasonic transmitter/receiver device 21C of the third example. As shown in FIG. 7*c*, the difference is that the common grounding wire 39*e* is arranged on the edge where two side surfaces are adjacent to each other in the mutually superposed transmission section and reception section, namely, on the edge far from the arrangement positions of the transmission signal wire 38*e* and the reception signal wire 37*e* in planar view, among the edges located on both ends of the first side surface 21*a*.

Similarly to the ultrasonic transmitter/receiver device 21A of the first example, the ultrasonic transmitter/receiver device 21F of the sixth example is designed in the form of a quadrangular prism, and includes a rectangular input/output surface for inputting and outputting the ultrasonic wave, and four first through fourth side surfaces 21*a*, 21*b*, 21*c* and 21*d* perpendicular to this input/output surface. As shown in FIG. 7*d*, the difference of the ultrasonic transmitter/receiver device 21F of the sixth example is found in that the reception signal wire 37*f* is arranged on the edge where two side surfaces are adjacent to each other in the mutually superposed transmission section and reception section, namely, on the edge far from the arrangement positions of the transmission signal wire 38*f* and the common grounding wire 39*f*, in planar view, among the edges located on both ends of the third side surface 21*c*.

The ultrasonic transmitter/receiver device 21K of the seventh example is approximately the same as the ultrasonic transmitter/receiver device 21F of the sixth example. As shown in FIG. 7*e*, the difference is found in that the transmission signal wire 38*k* is located on the edge where two side surfaces are adjacent to each other in the mutually superposed transmission section and reception section, namely, on the edge far from the arrangement positions of the reception signal wire 37*k* and the common grounding wire 39*k*, in planar view, among the edges located on both ends of the fourth side surface 21*d*.

The ultrasonic transmitter/receiver device 21M of the eighth example is approximately the same as the ultrasonic transmitter/receiver device 21F of the sixth example. As shown in FIG. 7*f*, the difference is found in that, in the ultrasonic transmitter/receiver devices 21M arranged in a two-dimensional array with "m" rows and "n" columns, the ultrasonic transmitter/receiver device 21M in the rows adjacent to each other is characterized by the transmission signal wire 38*m* and reception signal wire 37*m* being arranged alternately with each other. To put it another way, in the ultrasonic transmitter/receiver device 21M of a certain column, the reception signal wire 37*m* is arranged on the edge where two side surfaces are adjacent to each other in the mutually superposed transmission section and reception section, namely, on the edge far from the arrangement positions of the transmission signal wire 38*m* and common grounding wire 39*m*, in planar view, among the edges located on both ends of the third side surface 21*c*. In the ultrasonic transmitter/receiver device 21M in the column adjacent to the certain column, the transmission signal wire 38*m* is arranged on the edge where two side surfaces are adjacent to each other in the mutually superposed transmission section and reception section, namely, on the edge far from the arrangement positions of the reception signal wire 37*m* and common grounding wire 39*m*, in planar view, among the edges located on both ends of the third side surface 21*c*.

The ultrasonic transmitter/receiver device 21I of the ninth example is approximately the same as the ultrasonic transmitter/receiver device 21C of the third example. As shown in FIG. 7*g*, the difference is found in that, in the ultrasonic transmitter/receiver devices 21I arranged in a two-dimensional array with "m" rows and "n" columns, the ultrasonic transmitter/receiver device 21I in the rows adjacent to each other is characterized by the transmission signal wire 38*i* and reception signal wire 37*i* being arranged alternately with each other on the second side surface 21*b* and fourth side surface 21*d* (third side surface 21*c*), respectively. To be more specific, in the ultrasonic transmitter/receiver device 21I of a certain column, the transmission signal wire 38*i* is arranged along the superposition on the fourth side surface 21*d* (third side surface 21*c*), and the reception signal wire 37*i* is arranged along the superposition on the second side surface 21*b*. Further, in the ultrasonic transmitter/receiver device 21I of the column adjacent to the aforementioned certain column, the transmission signal wire 38*i* is arranged along the superposition on the second side surface 21*b*, and the reception signal wire 37*i* is arranged along the superposition on the fourth side surface 21*d* (third side surface 21*c*).

Thus, the ultrasonic transmitter/receiver devices 21A through 21I of the aforementioned structure of the first through ninth examples are characterized by wider wiring intervals (wherein each wire is arranged at a further position) and minimized cross talk between wires, as compared with the ultrasonic transmitter/receiver device 21J where the common grounding wire 39*j* is arranged on one side surface, for example, approximately at the center of the first side surface 21*a*, and the transmission signal wire 38*j* and reception signal wire 37*j* are arranged on the edges on both sides of the first side surface 21*a*, respectively, as shown in the Comparative Example of FIG. 8. From the viewpoint of reducing cross talk between wires, the ultrasonic transmitter/receiver device 21E of the fifth example shown in FIG. 7*c* is more preferably used because the wiring interval is the greatest. Thus, from the viewpoint of reducing cross talk and improving the performance, the ultrasonic probe 2 and ultrasonic diagnostic apparatus S equipped with the ultrasonic transmitter/receiver device 21E of the fifth example is preferable and the ultrasonic probe 2 and ultrasonic diagnostic apparatus S equipped with the ultrasonic transmitter/receiver device 21E of the fifth example is more preferably used.

In the present embodiment, the ultrasonic transmitter/receiver device 21 is designed in the form of a quadrangular prism. However, it can be designed in such a prismatic form as a triangular prism and hexagonal prism.

The following describes one of the methods of manufacturing the ultrasonic probe 2 equipped with the aforementioned ultrasonic transmitter/receiver device 21. This method approximately includes a step of forming a transmission section 32 on the sound absorbing layer 31, a step of installing an outgoing cable for each electrode layer of the transmission section 32 on the side surface of the transmission section 32, a step for forming a reception section 34 on the transmission section 32, a step of installing the outgoing cable for the electrode layer of the reception section 34 on the side surface of the reception section 34 and a step of forming an acoustic matching layer 35 and acoustic lens 36.

To put it more specifically, the wiring board is coated with a sound absorbing material so that a sound absorbing layer 31 is formed. An aluminum electrode layer is formed on the sound absorbing layer 31, for example, by the vapor deposition method, and is coated with the piezoelectric film made of such an inorganic piezoelectric material as PZT. Then an aluminum electrode layer is formed thereon for example, by the vapor deposition method. This procedure forms piezoelectric elements for one layer for transmission. In the present embodiment, this procedure is repeated three times and three layers of transmission section 32 are produced.

This is followed by the grooving step performed at a interval of 0.3 mm, for example, by the dicing saw, with the result that 8100 transmission arrays of 90 rows and 90 columns, for example, are formed. Then the wiring operation is performed for connecting the transmission signal wire 38. The groove having the transmission signal wire 38 installed thereon is filled with, for example, a polyimide resin which serves as a sound absorber and insulator.

This is followed by the wiring operation step for connection of the common grounding wire 39 to be arranged on the side surface of the transmission section 32. The transmission section 32 is coated, for example, with polyimide resin as the buffer layer 33.

Then an aluminum electrode layer is formed on the buffer layer 33, for example, by the vapor deposition method, and is coated with a piezoelectric film made of such an organic piezoelectric material as vinylidene polyfluoride. An aluminum electrode layer is formed thereon, for example, by the vapor deposition method. This procedure forms piezoelectric elements for one layer for reception. In the present embodiment, this procedure is repeated three times and three layers of reception section 34 are produced.

The groove cutting operation is performed by a dicing saw in such a way as to conform to the aforementioned grooves of the transmission section 32 in both the vertical and horizontal directions. This step forms a reception array indirectly laid through the buffer layer 33 on the transmission array. This is followed by the wiring operation step for connection with the reception signal wire 37. Then the groove having this reception signal wire 37 installed thereon is filled, for example, with polyimide resin.

This is followed by the wiring operation step for connection of the common grounding wire 39 to be arranged on the side surface of the reception section 34. The groove having the common grounding wire 39 installed thereon is filled, for example, with polyimide resin.

The acoustic matching layer 35 is formed and the acoustic lens 36 is then formed. Thus, the aforementioned process produces the ultrasonic probe 2 equipped with the aforementioned ultrasonic transmitter/receiver device 21.

The aforementioned production method provides comparatively easy production of an ultrasonic probe 2, even when there is an increase in the number of the ultrasonic transmitter/receiver devices 21 of the ultrasonic probe 2 to reduce the size of each ultrasonic transmitter/receiver device 21. This ensures production of the ultrasonic probe 2 at reduced costs with relatively high productivity.

To represent the present invention, the above description has given an appropriate and adequate explanation of the present invention with reference to the drawings using embodiments. It should be noted that those skilled in the art could easily perform modifications and/or improvements of the aforementioned embodiment. Thus, if the modifications or improvements made by those skilled in the art do not conform to the level departing from the scope of the invention claimed, such modifications or improvements are to be interpreted as being included in the present claims.

What is claimed is:

1. An ultrasonic transmitter/receiver device comprising:
   a laminate comprising a transmission section and a reception section superposed on each other, wherein:
   the transmission section comprises one or more first piezoelectric elements and is configured to transmit a first ultrasonic wave according to a transmission signal;
   the reception section comprises one or more second piezoelectric elements and is configured to output a reception signal generated by reception of a second ultrasonic wave; and
   the laminate has an emission/entry surface for emission and entry of the ultrasonic waves, and a plurality of side surfaces substantially perpendicular to the emission/entry surface;
   a set of transmission signal wire and transmission grounding wire for supplying the transmission signal to the transmission section; and
   a set of reception signal wire and reception grounding wire for picking up the reception signal from the reception section,
   wherein the transmission grounding wire and the reception grounding wire are integrated as a common grounding wire, and
   wherein the common grounding wire and the transmission signal wire are arranged on different side surfaces of the laminate, and the common grounding wire and the reception signal wire are arranged on different side surfaces of the laminate.

2. The ultrasonic transmitter/receiver device of claim 1, wherein the side surfaces of the laminate include an edge where two of the side surfaces intersect, and the common grounding wire is arranged on the edge.

3. The ultrasonic transmitter/receiver device of claim 1, wherein the side surfaces of the laminate include an edge where two of the side surfaces intersect, and the transmission signal wire is arranged on the edge.

4. The ultrasonic transmitter/receiver device of claim 1, wherein the side surfaces of the laminate include an edge where two of the side surfaces intersect, and the reception signal wire is arranged on the edge.

5. The ultrasonic transmitter/receiver device of claim 1, wherein the one or more second piezoelectric elements of the reception section is/are formed of an organic piezoelectric material.

6. An ultrasonic probe comprising a plurality of ultrasonic transmitter/receiver devices, each of the ultrasonic transmitter/receiver devices comprising:

a laminate comprising a transmission section and a reception section superposed on each other, wherein:
- the transmission section comprises one or more first piezoelectric elements and is configured to transmit a first ultrasonic wave according to a transmission signal;
- the reception section comprises one or more second piezoelectric elements and is configured to output a reception signal generated by reception of a second ultrasonic wave; and
- the laminate has an emission/entry surface for emission and entry of the ultrasonic waves, and a plurality of side surfaces substantially perpendicular to the emission/entry surface;

a set of transmission signal wire and transmission grounding wire for supplying the transmission signal to the transmission section; and a set of reception signal wire and reception grounding wire for picking up the reception signal from the reception section, wherein the transmission grounding wire and the reception grounding wire are integrated as a common grounding wire, and wherein the common grounding wire and the transmission signal wire are arranged on different side surfaces of the laminate, and the common grounding wire and the reception signal wire are arranged on different side surfaces of the laminate.

7. An ultrasonic diagnostic apparatus comprising an ultrasonic probe, the ultrasonic probe comprising a plurality of ultrasonic transmitter/receiver devices, each of the ultrasonic transmitter/receiver devices comprising:

a laminate comprising a transmission section and a reception section superposed on each other, wherein:
- the transmission section comprises one or more first piezoelectric elements and is configured to transmit a first ultrasonic wave according to a transmission signal;
- the reception section comprises one or more second piezoelectric elements and is configured to output a reception signal generated by reception of a second ultrasonic wave; and
- the laminate has an emission/entry surface for emission and entry of the ultrasonic waves, and a plurality of side surfaces substantially perpendicular to the emission/entry surface;

a set of transmission signal wire and transmission grounding wire for supplying the transmission signal to the transmission section; and a set of reception signal wire and reception grounding wire for picking up the reception signal from the reception section, wherein the transmission grounding wire and the reception grounding wire are integrated as a common grounding wire, and wherein the common grounding wire and the transmission signal wire are arranged on different side surfaces of the laminate, and the common grounding wire and the reception signal wire are arranged on different side surfaces of the laminate.

* * * * *